United States Patent [19]

Downer et al.

[11] 4,003,994

[45] Jan. 18, 1977

[54] COPPER-ALKALINE EARTH METAL FUNGICIDAL COMPOSITIONS

[75] Inventors: John D. Downer; Clarence A. L. Phillips, both of Trinidad, British W. Indies

[73] Assignee: Texaco Trinidad, Inc., Trinidad, British W. Indies

[22] Filed: Nov. 4, 1974

[21] Appl. No.: 520,512

Related U.S. Application Data

[63] Continuation-in-part of Ser. No. 360,504, May 15, 1973, abandoned.

[52] U.S. Cl. .................................. 424/157; 424/294
[51] Int. Cl.² .................... A01N 11/00; A01N 9/00
[58] Field of Search ........................... 424/157, 294

[56] References Cited

UNITED STATES PATENTS

| | | | |
|---|---|---|---|
| 993,827 | 5/1911 | Ellis | 424/294 |
| 1,679,919 | 8/1928 | Rogers et al. | 424/294 |
| 2,423,611 | 7/1947 | Minich | 424/294 |
| 2,423,619 | 7/1947 | Roon | 424/294 |
| 2,865,956 | 12/1958 | Ellis et al. | 260/504 |
| 2,938,828 | 5/1960 | van der Waarden et al. | 424/294 |
| 3,061,508 | 10/1962 | Morriss et al. | 424/294 |
| 3,111,456 | 11/1963 | Hochman et al. | 424/294 |
| 3,661,550 | 5/1972 | Downer et al. | 71/27 |

OTHER PUBLICATIONS

The Condensed Chem. Dict. — 6th ed. — Reinhold Publ. Corp., 1961 pp. 302.
The Merck Index 7th Ed. — pp. 161–162, Merck & Co. Inc. 1960.
The Condensed Chem. Dict., 6th Ed. — Reinhold Publ. Corp. 1961 — pp. 203.

*Primary Examiner*—Albert T. Meyers
*Assistant Examiner*—D. W. Robinson
*Attorney, Agent, or Firm*—T. H. Whaley; C. G. Ries; Henry W. Archer

[57] ABSTRACT

The invention discloses as new fungicidal compositions of matter dispersed micelles of overbased copper naphthenates in non-phytotoxic spray oils prepared metathetically. Each micelle contains a combined alkaline earth metal to reduce phytotoxicity of the dispersions. The alkaline earth metal may be present partly as naphthenate in the outer protective layer of the dispersed micelles. The inner core of the micelle is mainly copper hydroxide but some alkaline earth metal hydroxide may also be present. The mole percent of alkaline earth metal to copper ranges from about 1 to about 7 and the preferred metal is calcium. The micelles form clear fungicidal dispersions in spray oils.

6 Claims, No Drawings

COPPER-ALKALINE EARTH METAL FUNGICIDAL COMPOSITIONS

REFERENCE TO COPENDING APPLICATION

This application is a continuation-in-part of coassigned patent application Ser. No. 360,504 filed May 15, 1973 and now abandoned.

BACKGROUND OF THE INVENTION

1. Field of the Invention

The present invention is concerned with improved overbased copper fungicidal spray compositions containing an alkaline earth metal to reduce the phytotoxicity thereof.

As is well known most of the parasitic diseases of plants are caused by fungi. Practically every species of plant is more or less subject to attack by parasitic fungi. Fungi cause the greatest damage to crops.

The fungicidal agents most often used are sulphur, mercury, certain organic compounds and cooper. Copper fungicides have been known for several centuries. Just after the turn of the 17th Century the Abbé Prévost showed that fungous spores were prevented from germinating when they have been in contact with a solution of copper sulphate. However, water soluble copper compounds cannot be used on plants because the cupric ion is extremely toxic to plant life. Sparingly soluble derivatives of copper must be used for leaf application. Not all water insoluble compounds of copper are fungicidal and it is believed that the in vitro fungicidal activity of a copper compound is dependent largely on its solubility in spore exudate or other solubilizing substance associated with the plant itself. The mechanism by which copper enters solution from the dried, alkaline, well-known Bordeaux mixture is believed to be one of complex formation. It seems that the fungicidal action of cooper depends upon reaction in the fungal cell. Relatively little attention seems to have been given to oil soluble (water insoluble) derivatives of copper.

Since copper fungicides are usually insoluble in water they are applied in the form of powders or in relatively large volume aqueous suspensions and as such are readily removed by wind and rain necessitating applications at short intervals which is expensive.

It was suggested previously that this disadvantage might be overcome by using a non-phytotoxic carrier oil containing an oil soluble copper compound. In particular it was suggested that a spray oil in which the copper is solubilized as copper naphthenate would possess improved resistance to rain and wind, better contacting, and be cheaper.

A marketable clear fungicidal spray oil has yet to be developed. A fungicidal copper spray with increased activity and high resistance to rain is claimed in a patent to Farb. Bayer A.-G. (O. Telle and F. Grewe, Ger. Pat. No. 1,088,285/1957; Chem. Abs., 1962, 57, 5161i), the copper compound being mixed with magnesium soaps and fatty acid esters. A clay-oil emulsion of copper naphthenate is claimed (O. N. Yuganova, Chem. Abs., 1951, 45, 5351g) to stick to foliage. Certain petroleum oils used as supplements to fixed-copper spray formulations greatly improve the performance of the copper fungicide, the oil acting in part to increase the weathered copper deposit on the surface of the sprayed leaves (J. D. Wilson, Plant Disease Reptr., 1961, 45, 282; J. D. Wilson and O. K. Hedden, ibid, 1963, 47, 564; J. D. Wilson, The Pesticide News, Ohio, 1962, 15, 56). Oil-based copper fungicides in low volume were found (S. Screenivasan, Chem. Abs., 1969, 71, 37889p) superior to Bordeaux mixture and, by their ability to stick to the leaf, they resisted rain washing. The preparation of oil soluble copper xanthates for use as fungicides has been described by S. B. Tuwiner (U.S. Pat. No., 2,651,649/1953, to Phelps Dodge Corp.; Chem. Abs., 1954, 48, 8819d). The copper compounds suggested by these researchers are not economical enough to warrant widespread use. The less expensive copper naphthenate, usually in kerosine, has been used as a wood preservative (P. I. Smith, Soap, 1938, 14(11), 86; Chem. Abs., 1939, 33, 777[7]; B. C. Bera, Chem. Abs., 1963, 59, 3004a). Complex copper salts of sulphurized cresylic and naphthenic acids are claimed (A. J. Krus, U.S. Pat. No. 2,188,951, to Richards Chemical Works, Inc., Chem. Abs., 1949, 34, 3872[9]) for use as fungicides for trees and plants. Copper naphthenate paste has been suggested (N. V. Ptitsyna, et al., Chem. Abs., 1962, 56, 12033g; 1964, 61, 1196e) as a substitute for Bordeaux mixture.

It has been found, however, that neutral copper naphthenate carried in a non-phytotoxic carrier oil caused severe leaf burn when applied to grapefruit albeit at relatively large dosage and concentration. In co-assigned patent application Ser. No. 360,506 it is disclosed that overbased copper naphthenates in which the ratio of metal to naphthenic acid ranges from over 1 to 20 carried as a clear dispersion in spray oil are less phytotoxic because of the in-built buffer effect of the excess base. When applied to Valencia orange leaves at 0.1% w/v copper and at a dosage of 12 gal./acre (low severity) the spray oil solution of a nominal 1000% overbased copper naphthenate was found to be almost completely nonphytotoxic. However, when tested at a higher concentration of copper (1% w/v) and higher application level (250 gal./acre, high severity) the 1000% overbased copper naphthenate spray oil caused severe leaf burn. This result was unexpected since neither zinc nor manganese overbased naphthenates had been found phytotoxic at the high severity applications. It was noted that the severity of leaf burn caused by the foliar sprays increased with increasing concentration of the overbased copper naphthenate. Thus the phytotoxicity of the overbased copper naphthenate spray oil was found to depend on the concentration of copper in the spray oil as well as the quantity of oil applied. In contrast to overbased zinc and manganese naphthenates the overbased copper naphthenate spray oil applied at high severity dosage is definitely phytotoxic. At low severity but still practical dosages the spray oil is relatively non-phytotoxic to citrus. But it is evident that a spray oil containing overbased copper naphthenate alone would be restricted to a low concentration of copper.

SUMMARY OF THE INVENTION

It has been discovered in accordance with the invention that the phytoxicity of overbased copper naphthenates spray oils can be substantially reduced by incorporating therein of at least one alkaline earth metal, e.g., calcium. Two types of copper-alkaline earth metal overbased naphthenates are possible. One type, in which the copper and alkaline earth metal are in the same micelle, was until now unknown; it is made metathetically as disclosed below. The other type of copper-alkaline earth metal overbased naphthenates is that in which the copper and the alkaline earth metal are in separate micelles, and is made by blending copper overbased naphthenates with alkaline earth metal overbased naphthenates in the desired proportions in spray oil. The individual overbased naphthenates required for blending can be made according to the patent application Ser. Nos. 360,505 and 360,506. In the blends of copper naphthenates and calcium (or alkaline earth metal) overbased naphthenates in spray oil the copper containing micelle will consist of an outer protective layer of copper naphthenate and a core of copper hydroxide; the calcium containing micelle will have an external protective layer of calcium naphthenate and a core of calcium hydroxide. In the type in which each micelle contains both copper and calcium, as obtained by the method described in this application, the calcium may be present partly as naphthenate in the outer protective layer of the dispersed micelle; the inner core of the micelle will be mainly copper hydroxide but some calcium hydroxide may be present.

In accordance with this invention, highly overbased oil soluble copper-alkaline earth metal naphthenates sprays are prepared as more fully hereinafter described, by forming copper-alkaline earth metal naphthenates and dissolving same in horticultural spray oil, the ratio of equivalents of copper to naphthenate being from over 1 to 20 and the mole percent of alkaline earth metal to copper being from 1 to about 8. Such oils are applied at the rate of about 0.5 to 10 gals of spray oil dispersion per acre at a concentration of 0.025 to 1.0% of copper to the foliage or branches of plants and are effective fungicides, e.g., against coffee rust, without being phytotoxic.

Overbased salts and their methods of preparation have been discussed in the co-assigned patent application Ser. Nos. 360,505/6. There are at least five general methods for preparing overbased salts. For example, U.S. Pat. No. 2,865,956 to Ellis describes highly basic salts to naphthenac acids made by direct carbonation, the excess base in the micelles formed being in the form of metal carbonate. The method of preparing the novel copper-alkaline earth metal overbased naphthenates disclosed in this application is a metathetical one using alkali hydroxide, the excess base in the micelles formed being in theform of metal hydroxide. The metathetical method is of more general application and therefore preferred.

In preparing the subject compositions an alcoholic solution of a copper inorganic salt and of an alkaline earth metal inorganic salt, and an alcoholic solution of alkali hydroxide are added to a stirred solution of naphthenic acids in a light hydrocarbon diluent of higher boiling point than the alcohol used for dissolving the inorganic salt. The total equivalents of the two salts equal that of the alkali hydroxide. The alcohol and any water are then removed by distillation, carrier oil added and the light hydrocarbon solvent removed by distillation. When methanol is used the reaction is conveniently carried out at ambient temperature but temperatures up to 60° C may be employed without adversely affecting the yield, stability or basicity of the product. The methanolic inorganic salts and methanolic alkali hydroxide are preferably added separately but simultaneously over 1 hour.

The inorganic salts used in the preparation of the overbased salts by the metathetical method are common salts such as chloride, sulphate, nitrate, etc., soluble in the lower alkanols such as methanol; water may be added to assist solubilization.

Sodium hydroxide is the preferred alkali hydroxide but other alkali hydroxides such as potassium hydroxide may be used.

The naphthenic acids employed in the preparation of the overbased salts of the present invention are aliphatic cyclic hydrocarbon carboxylic acids that are usually obtained by treating a naphthenic crude oil or fractions thereof with a caustic solution to form naphthenates that are soluble in aqueous solution. Such acids are described in greater detail in Kirk-Othmer, "Encyclopedia of Chemical Technology," Interscience Encylcopedia Co., 1952, Vol. 9, starting at page 241. For the purpose of the present invention, acids having a molecular weight in the range of 200 to 600, should be used. These acids can also be characterized by their acid values expressed in terms of milligram equivalents of KOH. The acids may require to be deoiled and distilled before use if significant amounts of phenolic materials are present.

The alcohols used with the sodium hydroxide and copper-alkaline earth metal chlorides in the preparation of the subject salts comprise lower alkanols and preferably methanol.

The light hydrocarbon diluent used with the naphthenic acids in preparing the overbased copper-alkaline earth metal naphthenates is preferably a hydrocarbon, such as benzene, toluene and xylene which is a liquid with a low viscosity at room temperature including other aromatic solvents boiling up to about 149° C. provided their viscosity is not too high. The quantity of solvent to be used will be determined by the solubility of the particular naphthenic acids used.

The horticultural spray oil used here in a hydrocarbon mineral oil having a gravity API of 31–36; a viscosity at 100°F. of 81 to 87 Saybolt Universal Seconds and a boiling point range between about 600° to 775° F. An analysis of a preferred oil sample is given in Table I. However for normal applications highly refined carrier oils, predominantly paraffinic, having a minimum API gravity of 27, viscosity at 100° F of between 55 and 100 Saybolt Universal Seconds, boiling range of 600°–775° F. and minimum unsulphonated residue of 85%, would be suitable. A lighter oil with API gravity around 50 and boiling range 85°–600° F. belonging to the general groups of paraffins, isoparaffins and/or naphthenes might be desirable for use with light weight ultra low volume sprayers. Where desired the spray oil solution can be emulsified with water for so-called moderate volume applications (2–20 gal./acre).

It will be noted by those skilled in this art that at least some of the oils emcompassed by the above definitions have pesticidal, acaricidal, insecticidal and/or virucidal activities and that such properties are retained in the claimed compositions which contain such materials. Accordingly these compositions have multiple effects.

TABLE I

ANALYSIS OF OIL USED AS CARRIER FOR OVERBASED COPPER NAPHTHENATES

| Sample No. | RS-1200/67 |
|---|---|
| Sp. Gravity at 60° F. (ASTM D-1298) | 0.8493 |
| ° API Gravity (ASTM D-1250) | 35.1 |
| Flash Point, (COC), ° F (ASTM D-92) | 395 |
| Viscosity SSU/100° F (ASTM D-445/2161) | 84.2 |
| Colour (ASTM D-1500) | 0.5 |
| Pour Point, ° F (ASTM D-97) | 5 |
| Neutralization No. mg.KOH/g. | 0.04 |
| Distillation ° F | |

TABLE I-continued

ANALYSIS OF OIL USED AS CARRIER FOR OVERBASED COPPER NAPHTHENATES

| | |
|---|---|
| IBP | 637 |
| 10% | 675 |
| 50% | 696 |
| 90% | 729 |
| FBP | 745 |
| Ash, % wt. | 0.001 |
| Unsulphonatable Residue, vol. % (ASTM D-483) | 94.2 |

DESCRIPTION OF SPECIFIC EMBODIMENTS

The following data and examples illustrative the preparation of the novel overbased copper-alkaline earth metal naphthenates of the present invention and their specific utility as fungicides in certain horticultural spray oils. It will be understood however, that it is not intended to limit the invention to the features thereof particularly exemplified hereinbelow nor to the metathetical method employed.

EXAMPLE I

The sample were prepared incorporating 0, 1, 4 and 7 mole % calcium chloride relative to copper chloride in the reaction mixture according to the following procedure: A solution of naphthenic acids, A.V., 138 mg.KOH/g., 26 g., 64 m.eq. in xylene (440 g.), was placed in a 2-liter three-necked flask equipped with stirrer and two dropping funnels. Solutions of sodium hydroxide (28 g., 704 m.eq.) in methanol (256 g.) and anhydrous or dehydrated cupric chloride and calcium chloride (704 m. eq. together) in methanol (256 g.) were added dropwise and simultaneously over a period of 1 hour through the dropping funnels to the well stirred mixture at ambient temperature. When the addition was completed stirring was continued for 30 minutes. The methanol, water and a little xylene were removed by distilling to a vapor temperature of 140° C. After cooling, the residue was filtered through a slurry of Celite in the carrier oil to be used (Table I). Finally, the carrier oil (220 g.) was added and the xylene removed under vacuum using a rotary film evaporator, leaving a clear dispersion of the overbased copper/calcium naphthenate in the carrier oil.

Analysis: A known volume (ca. 5 ml.) of the carrier oil formulation was diluted in xylene and decomposed with 1:1 hydrochloric acid. The xylene-naphthenic acid layer was washed well with saturated brine solution to remove all mineral acid and the washings added to the aqueous layer. The washed xylene-naphthenic acid layer was titrated with N/10 standard aqueous sodium hydroxide solution to phenolphthalein end-point (using a known amount of isopropylalcohol to aid de-emulsification), and the naphthenic acid content expressed in m.eq./100 ml. The aqueous layer was analyzed for copper by an atomic absorption spectrophotometer. Results are given in Table II.

Spray oils with the overbased copper naphthenate containing 0.0, 1.6, 4.0 and 8.0 mole % calcium relative to copper (Table II) were screened for non-phytotoxicity as described below. Observations on the incidence of leaf-burn made at 3 and 10 days after spraying are given in Table III. Only the spray oil containing overbased copper naphthenate with 4 mole % calcium relative to copper (preparation 3, Table II) at 0.125% wt. copper was non-phytotoxic to Grapefruit. The spray oil containing overbased copper naphthenate with 1.6 mole % calcium relative to copper (preparation 2, Table II) showed only very slight burns at 0.125% wt. copper. These data indicate that phytotoxicity is reduced by incorporation of calcium into the micelle of the overbased copper naphthenate spray oil.

Screening tests were made with the overbased metal naphthenates, preparations 1, 2, 3 and 4 (Table I). Each spray formulation was applied at three concentrations of copper, viz. 0.5, 0.25, and 0.125 wt. percent. An aerosol dispenser was used for applying the sprays to the grapefruit twigs containing cluster of about 30 leaves. Spraying was for about 1½ seconds in each operation. Observations on the incidence of leaf burn were made at 3 and 10 days after spraying. Results are given in Table III.

TABLE II

PREPARATION OF OVERBASED COPPER NAPHTHENATES AND MIXED OVERBASED COPPER/CALCIUM NAPHTHENATES: ANALYSES

| Prep. No. | Ca/Cu % Ratio (equiv.) Reactants | Ca/Cu % Ratio (equiv.) Product | Yield g. | Copper Content m.eq./100 ml. | Copper Content g./100 ml. | Naphthenic acid m.eq./100 ml. | Overbasicity* % |
|---|---|---|---|---|---|---|---|
| 1 | No Ca | No Ca | 269 | 245.4 | 7.8 | 23.15 | 1060 |
| 2 | 1 | 1.6 | 274 | 248.5 | 7.9 | 23.2 | 1070 |
| 3 | 4 | 4.0 | 284 | 232.8 | 7.4 | 23.3 | 1000 |
| 4 | 7 | 8.0 | 268 | 191.9 | 6.1 | 22.3 | 860 |

*Ratio (equiv.) Copper:Naphthenic acid × 100.

TABLE III

LEAF BURN INCIDENCE IN RELATION TO SPRAY TREATMENT ON GRAPEFRUIT OBSERVED AT 3 and 10 DAYS RESPECTIVELY

| Overbased Naphthenate Formulation (Table I) % Ratio (equiv.) Ca/Cu | Leaf Burn Score* 0.5% wt. Cu 3 days | 0.5% wt. Cu 10 days | 0.25% wt. Cu 3 days | 0.25% wt. Cu 10 days | 0.12% wt. Cu 3 days | 0.12% wt. Cu 10 days |
|---|---|---|---|---|---|---|
| 0.0 (prepn. 2) | 3 | 3 | 3 | 3 | 3 | 3 |
| 1.6 (prepn. 3) | 2 | 2 | 2 | 2 | 1 | 1 |
| 4.0 (prepn. 4) | 1 | 2 | 1 | 2 | 0 | 0 |
| 8.0 (prepn. 5) | 3 | 3 | 2 | 2 | 2.5 | 3 |

*Leaf Burn Score  0 = none
 1 = slight

TABLE III-continued

LEAF BURN INCIDENCE IN RELATION TO
SPRAY TREATMENT ON GRAPEFRUIT
OBSERVED AT 3 and 10 DAYS RESPECTIVELY

| Overbased Naphthenate Formulation (Table I) | Leaf Burn Score[a] | | | | | |
|---|---|---|---|---|---|---|
| | 0.5% wt. Cu | | 0.25% wt. Cu | | 0.12% wt. Cu | |
| % Ratio (equiv.) Ca/Cu | 3 days | 10 days | 3 days | 10 days | 3 days | 10 days |

2 = moderate
3 = severe

The compositions of this invention are particularly effective against the following fungi: *Mycosphaerella musicola* (banana leaf spot disease), *Hemileia vastatrix* (coffee rust disease), *Mycosphaerella hori* (citrus greasy spot disease) and *Diapothe citri* (citrus melanose disease).

The subject spray oils preferably are added with a low volume motorized knapsack sprayer. A suitable droplet size for this type of application is about 80 microns but this size can be within the range of about 50 to about 100 microns. Experience has shown that a density of about 32 droplets per cm$^2$ is advantageous. Spraying is preferably done early in the wet season and when the weather in calm to minimize drifting of the oil spray.

The present compositions are particularly applicable for low volume spraying and are effective fungicides agaist coffee rust disease even when applied at the rate of 0.02 g/coffee per plant.

What is claimed is:

1. A fungicidal composition in the form of a micelle, said micelle comprising an outer protective layer consisting of the overbased copper-alkaline earth metal naphthenates of naphthenic acids having a molecular weight in the range of about 200 to about 600, and an inner core consisting mainly of copper hydroxide, the ratio of equivalents of copper to naphthenate ranging from about 1 to about 20, the mole percent ratio of said alkaline earth metal to copper being from 1 to 8.

2. The salt of claim 1, wherein said inner core contains some alkaline earth metal hydroxide.

3. A fungicidal oil spray composition particularly effective against *Mycosphaerella musicola*, *Mycosphaerella hori*, *Hemileia vastatrix* and *Diapothe citri* containing overbased copper-alkaline earth metal naphthenates, as defined in claim 1, and a non-phytotoxic hydrocarbon mineral oil carrier having a minimum gravity API of 27; a viscosity at 100° F. of between 55 and 100 Saybolt Universal Second; a boiling range between about 600° and 775° F. and a minimum unsulphonated residue of 85%; said copper being present in said oil at a concentration of between about 0.025 and about 1.0 percent.

4. The composition of claim 1, wherein the concentration of copper in said carrier oil ranges from 0.025 to 0.10 percent and said alkaline earth metal is calcium.

5. A method of protecting plants from fungi of the group of *Mycosphaerella musicola*, *Mycosphaerella hori*, *Diapothe citri* and *Hemileia vastatrix*, comprising spraying the leaves, branches or barks of said plants with from 0.5 to 20 gallons per acres of the composition of claim 3.

6. The method of claim 5, wherein at least 0.02 g. of copper per plant is supplied.

* * * * *